United States Patent
Kullik

Patent Number: 5,875,783
Date of Patent: Mar. 2, 1999

[54] GAS DELIVERY MEANS FOR RESPIRATORS AND ANESTHESIA APPARATUS

[75] Inventor: Götz Kullik, Lübeck, Germany

[73] Assignee: Drägerwerk AG, Lübeck, Germany

[21] Appl. No.: 965,256

[22] Filed: Nov. 6, 1997

[30] Foreign Application Priority Data

Apr. 9, 1997 [DE] Germany .......................... 19714664.9

[51] Int. Cl.⁶ .................................................. A61A 16/00
[52] U.S. Cl. ............................... 128/204.18; 128/204.21; 128/204.22; 415/206
[58] Field of Search ........................ 128/204.18, 204.21, 128/204.22, 205, 203.12, 205.25, 204.23; 415/206; 416/238

[56] References Cited

U.S. PATENT DOCUMENTS

| 4,686,975 | 8/1987 | Naimon et al. | 128/204.23 |
| 5,551,419 | 9/1996 | Ryoehlich | 128/204.23 |
| 5,603,315 | 2/1997 | Sasso, Jr. | 128/204.18 |
| 5,626,461 | 5/1997 | Rose | 415/206 |
| 5,694,926 | 12/1997 | DeVries et al. | 128/204.18 |

FOREIGN PATENT DOCUMENTS

| WO 87/10599 | 3/1987 | WIPO | 128/204.18 |
| WO 96/11717 | 4/1996 | WIPO | 128/204.18 |

*Primary Examiner*—John G. Weiss
*Assistant Examiner*—Charles W. Anderson
*Attorney, Agent, or Firm*—McGlew & Tuttle

[57] ABSTRACT

A gas delivery arrangement for respirators and anesthesia apparatus includes a radial flow compressor (10) with bent-backwards blades. The compressor impeller (11) is arranged in a stationary housing (14). The gas inlet (12) is located in the area of the axis of rotation of the compressor impeller (11) and the blades (13) extend from the gas inlet (12) in the area of the axis of rotation to the circular outer edge of the compressor impeller (11) and end there nearly tangentially. The free gas flow path between the outer edge of the compressor impeller (11) and the inner wall of the housing (14) passes over into the gas outlet (15) of the gas delivery arrangement in the direction of gas flow. The compressor impeller is driven by an electric motor and has a radius of up to 40 mm and a mass moment of inertia of up to about $4 \times 10^{-6}$ kg×m². The arrangement is an extremely compact gas delivery arrangement, which requires few components and no valves, can be used in a versatile manner and is able to change pressures in a highly dynamic manner, is provided by the subject of the present invention. The pneumatic resistance of the gas delivery arrangement according to the present invention is less than 4 mbar at a gas flow rate of 60 L per minute.

11 Claims, 7 Drawing Sheets

GAS DELIVERY MEANS FOR RESPIRATORS AND ANESTHESIA APPARATUS

FIELD OF THE INVENTION

The present invention pertains to a gas delivery means for respirators and anesthesia apparatus in the form of a radial flow compressor with blades bent backwards.

BACKGROUND OF THE INVENTION

Such radial flow compressors have been known, in principle, and special designs of such radial flow compressors have also been proposed for respirators.

WO 87/01599 shows a radial flow compressor, which is driven by pressurized oxygen in order to pump an oxygen-air mixture to the patient. Electrically driven respirators or anesthesia apparatus without pressurized gas supply for intermittent respiration use mostly either reciprocating pumps or continuously operating compressors with valve control. Large-volume reciprocating pumps are unable to follow the spontaneous breathing of patients rapidly enough, and small pistons operated at high frequency generate undesired pulsations in the breathing gas. Continuously operated compressors require an external pneumatic circuit with valves and are therefore technically complicated; in addition, the increase in the temperature of the breathing gas is undesirable. In addition, there are devices which operate as double-flow side-channel compressors based on a special principle of action and permit intermittent forms of exhalation without additional valves based on the manufacture of highly complicated individual parts, and they comprise many components. However, as a consequence of the greatly sloped pressure-flow characteristics of this type of compressor, the necessary properties can be obtained only by means of an expensive control of the characteristics and by the use of a microprocessor.

SUMMARY AND OBJECTS OF THE INVENTION

The primary object of the present invention is to provide a gas delivery means for respirators and anesthesia apparatus, which has a simple design, is extremely compact, requires no additional valve, is able to reach a predetermined pressure in the airways quickly and can be controlled so quickly that it can be used for supporting the spontaneous breathing of a patient.

According to the invention, a gas delivery device is provided for respirators and anesthesia apparatus in the form of a radial flow compressor with bent-backwards blades. The device includes a compressor impeller arranged in a stationary housing. A gas inlet is located in the area of the axis of rotation of the compressor impeller. The blades of the impeller extend from the gas inlet in the area of the axis of rotation to the circular outer edge of the compressor impeller and end essentially tangentially at the circular outer edge. The gas flow path between an outer wall of the compressor impeller and an inner wall of the housing passes over into a gas outlet in the direction of gas flow. The compressor impeller driven by an electric motor has a radius of up to 40 mm and a mass moment of inertia of up to about $4 \times 10^{-6}$ kg×m².

The gas delivery device preferably provides that the blades of the radial flow compressor, of which there are at least 6 and preferably 8 to 12, have a height of at least 4 mm in parallel to the axis of rotation of the compressor impeller. The compressor impeller preferably has a radius of up to 25 mm and a mass moment of inertia of up to about $2 \times 10^{-6}$ kg×m².

The gas delivery device is preferably used in a differential pressure range of up to 100 mbar, measured between the gas inlet in the area of the axis of rotation of the compressor impeller and the gas outlet, at a gas volume flow rate of up to 200 L per minute.

The gas delivery device may be arranged in a respirator. This may be by connecting the device to a gas storage space arranged upstream of the device, with connection to the ambient air. An oxygen feed is preferably provided between the storage space and the radial flow compressor via a line. The device is provided with a downstream flow sensor with a radial flow compressor electronic unit belonging to it for controlling the radial flow compressor, and it is connected to the patient via a nonreturn valve with a downstream exhalation valve. There is preferably a connection to the ambient air via a nonreturn valve connected to an exhalation valve for exhalation by the patient.

The device may be arranged in a respirator, connected to a gas storage space arranged upstream of it with connection to the ambient air. An oxygen feed is preferably provided between the storage space and the radial flow compressor via a line. The device is preferably provided with a downstream flow sensor with a radial flow compressor electronic unit belonging to it for controlling the radial flow compressor. An inhalation line is preferably provided joining the flow sensor and having a nonreturn valve to the patient as well as with an exhalation line with nonreturn valve to an exhalation valve, through which only exhaled gas flows and is connected to the ambient air as well as to the outlet of the radial flow compressor.

The gas delivery device may also be arranged in an anesthesia apparatus, provided with a fresh gas line with nonreturn valve to the radial flow compressor. A flow sensor with a radial flow compressor electronic unit belonging to it is preferably arranged downstream of the radial flow compressor for controlling the radial flow compressor. The flow sensor is joined by an inhalation line with a nonreturn valve to the patient. An exhalation line with the nonreturn valve is connected to the exhalation valve, which is connected for exhalation by the said patient to an anesthetic gas escape line via at least one nonreturn valve and, in parallel thereto, to the said fresh gas line via a manual respiration bag as well as a said carbon dioxide absorber.

The gas delivery device may also be arranged in an anesthesia apparatus, wherein both a fresh gas line with a nonreturn valve and with a manual respiration bag as well as a anaesthetic gas escape line with a nonreturn valve and with a parallel flow resistance on the inlet side are arranged upstream of the radial flow compressor. A flow sensor with a radial flow compressor electronic unit belonging to it for controlling the radial flow compressor as well an inhalation line leading to the patient with a carbon dioxide absorber and with a nonreturn valve as well as an exhalation line leading away from the patient with a nonreturn valve are preferably arranged downstream of the radial flow compressor on the outlet side.

One advantage of the present invention is that no pressurized gas supply is needed for the use of the gas delivery means according to the present invention. Another essential advantage of the present invention is the fact that an extremely compact radial flow compressor is provided, which comprises a few components, some of which are commercially available, and which makes it possible to cover a broad range of speeds of rotation and a broad pressure range in a few milliseconds via the control of the electric drive motor. Based on these properties, the gas delivery means according to the present invention is suitable for use for greatly different practical applications in the respiration of patients, in anesthesia apparatus and respirators alike. Various exemplary embodiments of the gas delivery means according to the present invention and its use for anesthesia or respiration will be explained on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
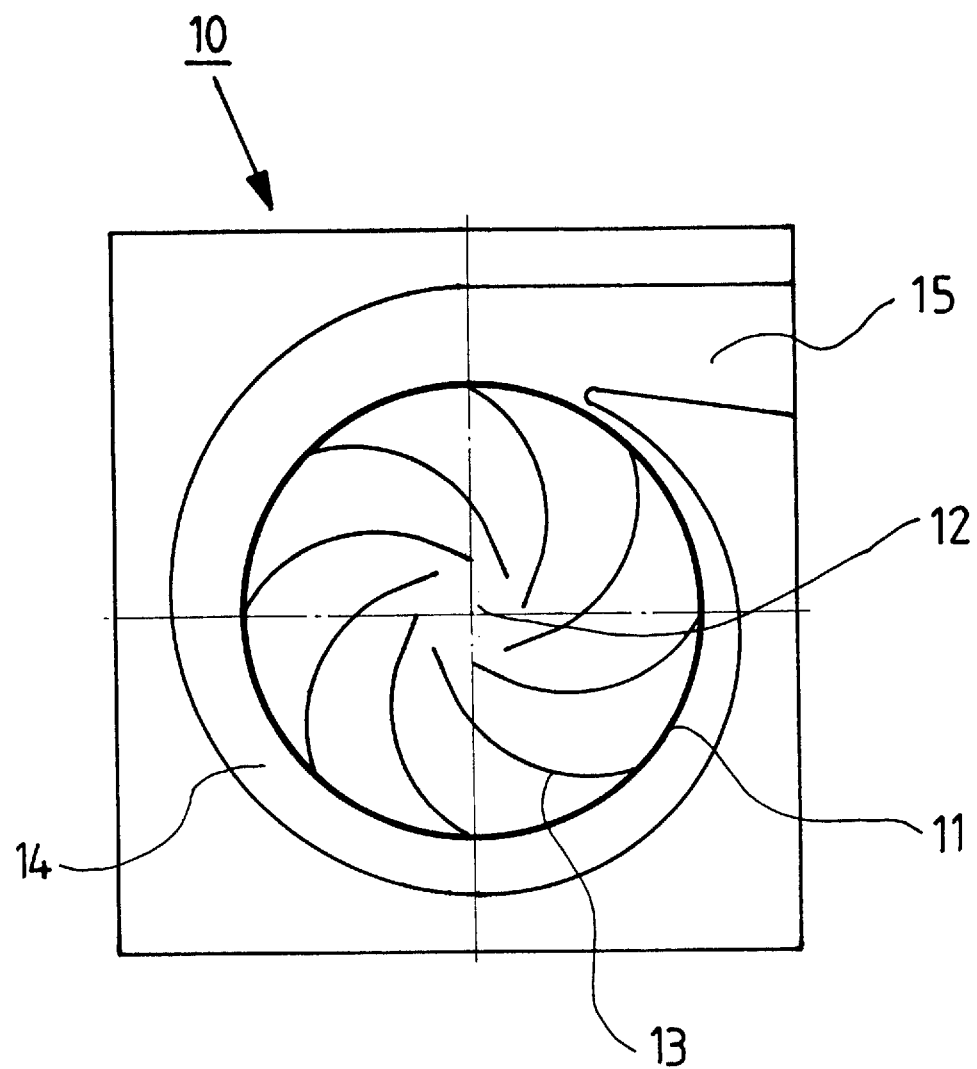
FIG. 1 is the sectional view of an embodiment of a radial flow compressor according to a schematic present invention.

Referring to the drawings in particular, the invention comprises a device including a gas delivery device. FIG. 1 shows the sectional view of a radial flow compressor 10 as the gas delivery device according to the present invention. The compressor impeller 11 rotates clockwise, the gas is drawn in through the gas inlet 12 in the area of the axis of rotation and is accelerated to the outside via the blades 13, which are bent backwards, and the centrifugal field. The gas is decelerated in the stationary housing 14 and in the gas outlet 15, and the pressure is increased. The stationary housing 14 is designed as a spiral housing. The gas outlet 15 is designed as a diffusor. In the exemplary embodiment, the bent-backwards blades 13 are on a flat impeller disk made of aluminum or plastic with a wall thickness of about 1 to 2 mm. The axis of rotation is arranged centrally on the impeller disk, and the gas inlet 12 is located in the area of the axis of rotation from one side through a gas duct. The compressor impeller 11, i.e., the impeller disk with the blades 13, is closed by plane-parallel plates at the distance of the rotating impeller disk with the blades 13 and the housing 14 with the gas outlet 15. To reach rapid changes in pressure of about 1 mbar per msec, which are necessary for use in respiration or anesthesia, it was determined that the radius of the compressor impeller 11 must not be larger than about 40 mm, and the mass moment of inertia of the compressor impeller 11 reaches up to about $4 \times 10^{-6}$ kg×m² (the mass moment of inertia of the compressor impeller 11 is less than or equal to about $4 \times 10^{-6}$ kg×m²). For especially compact applications, the radius of the compressor impeller 11 is not larger than about 25 mm, and its mass moment of inertia does not exceed about $2 \times 10^{-6}$ kg×m². Using a brushless, electronically commuted d.c. motor, a drive is manufactured, whose life is limited by the bearing only, and whose individual pneumatic components can be all cast or injection molded in very simple "Open-Closed molds." The simple design of the components, through which the gas flows, makes it possible to remove these parts in the field and to clean, sterilize and reinstall them, so that use in the patient part of an anesthetic gas system is possible. The characteristics of the radial flow compressor 10 are highly advantageous for use in the respiration system in intensive-care respiration and anesthesia (see FIG. 2). This property of the radial flow compressor 10 is achieved, among other things, by a marked backwards bending of the blades 13 on the impeller disk. The blades 13 end nearly tangentially at the outer circumference of the compressor impeller 11, i.e., deviating from the tangent in a range of up to 20°, preferably about 10°. The slight reduction in pressure during the delivery of the gas flows needed for respiration makes it possible to obtain all pressure-controlled breathing patterns via a very simple control of the speed of rotation. The control of the speed of rotation is thus simple, because the electronically commuted motor has speed sensors for controlling its rotating field. The system is completely open, i.e., the patient can breath spontaneously as desired at any pressure level. The system is also open when the compressor impeller 11 has stopped, so that no air valve is necessary. To obtain the property of "full-range open respiration," the pressure drop of the radial flow compressor 10 is less than 4 mbar at a flow rate of 60 L per minute and with the compressor impeller 11 not running. As was shown by experiments, a blade height of at least about 4 mm in the middle, rounding of the flow deflection at right angles at the air intake fitting for the gas inlet 12, and a slim diffusor as a gas outlet 15 with an opening angle of up to 6° are of significance in this connection. On the whole, an extremely variable gas delivery device in the form of a radial flow compressor 10 is provided, which can be used in a versatile manner as a dynamically speed-variable drive of a respirator or anesthesia apparatus.

Figure 2:
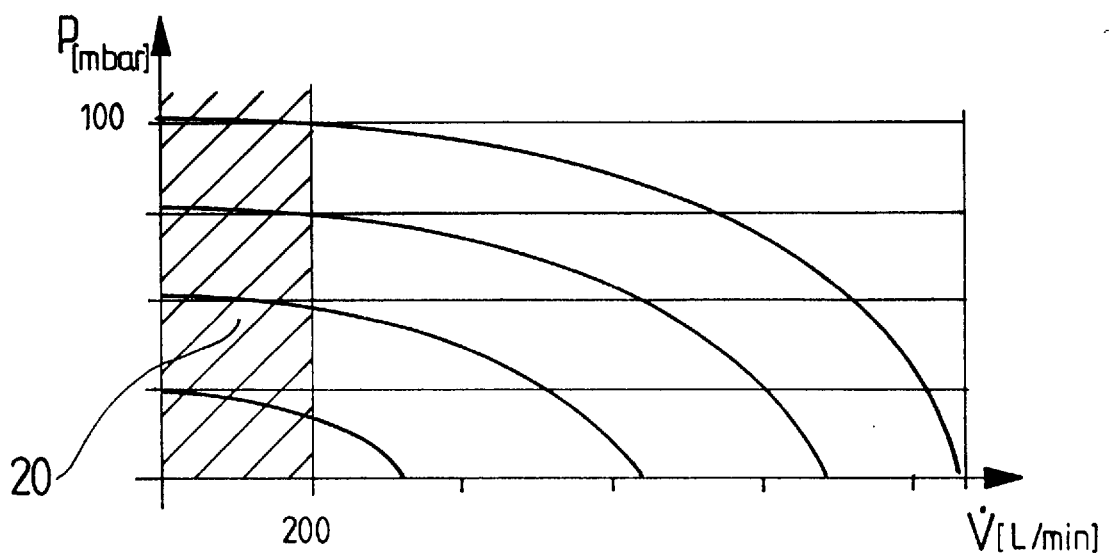
FIG. 2 is the characteristic diagram of a radial flow compressor according to the present invention.

FIG. 2 shows the characteristic diagram of a radial flow compressor 10. The differential pressure between the gas inlet 12 in the area of the axis of rotation and the gas outlet 15 is plotted as a function of the flow through the radial flow compressor 10 for four different speeds. The shaded area 20 shows the pressures (0 to 100 mbar) and flows rates (0 to 200 L per minute) needed in respirators. It can be recognized that the characteristics are nearly horizontal in the range of interest, i.e., the pressure depends practically only on the speed of rotation rather than on the flow rate.

Figure 3:
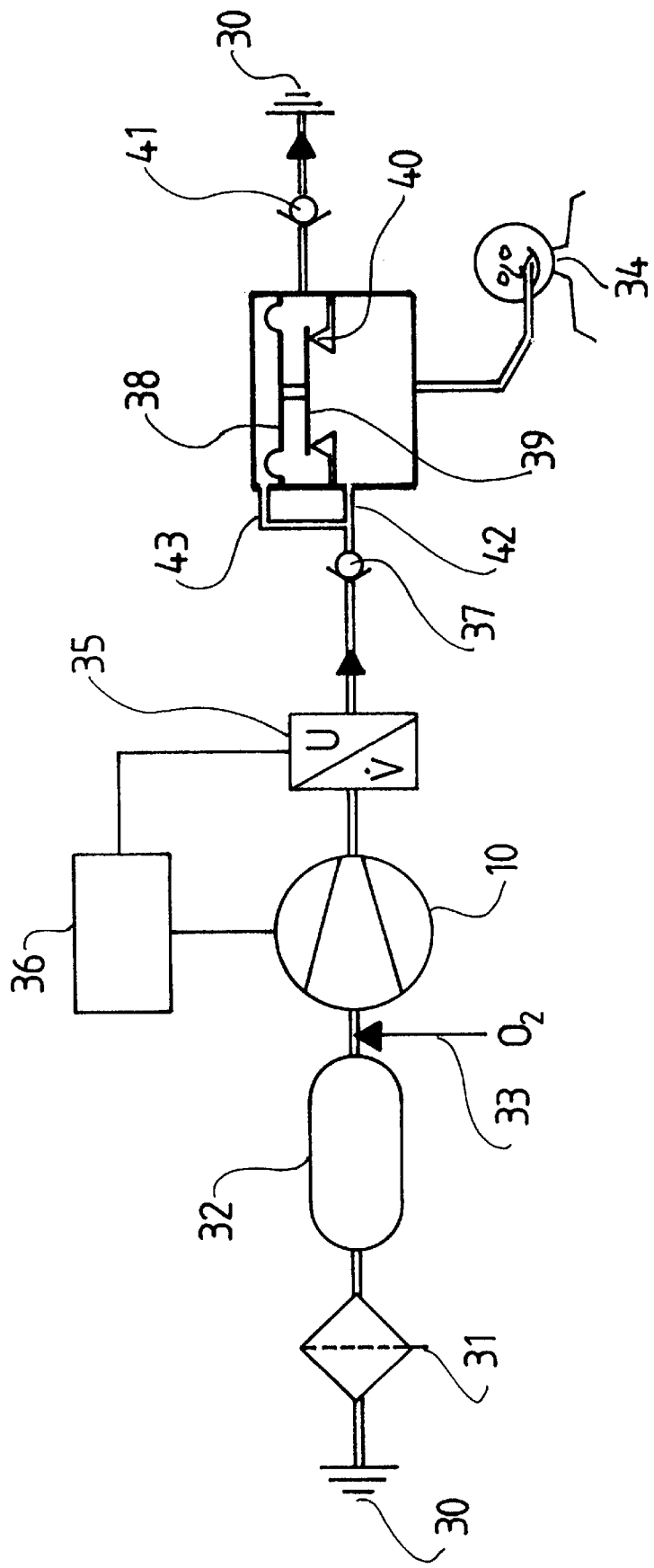
FIG. 3 is the circuit of a radial flow compressor according to the present invention for use in emergency respiration or in a respirator for domestic use.

FIG. 3 shows a circuit of the radial flow compressor 10 for use in emergency medicine or in home care. The radial flow compressor 10 draws ambient air from the atmosphere 30 via a bacteria filter 31 and a gas storage space 32. Oxygen is introduced continuously in the pressureless state via the line 33. Since the radial flow compressor 10 is not delivering during the exhalation by the patient 34, the oxygen being delivered during this time flows into the gas storage space 32 and is available for the next inhalation stroke. The inhalation flow is measured in the flow sensor 35, and the measured values may be used to control volume-based forms of respiration in the compressor electronic unit 36 with drive motor. The inhaled gas enters the patient 34 through a nonreturn valve 37 if the pressure in the inhalation line 42 and in the control line 43 is higher than in the patient's lungs, because the diaphragm 38 presses the valve disk 39 onto the crater (valve seat) 40 in this case. As soon as the pressure ratios between the inhalation line 42 and the patient 34 reverse either due to a reduction in the speed of rotation of the radial flow compressor 10 or due to an exhalation effort on the part of the patient 34, the valve disk 39 opens, and the patient 34 can exhale into the atmosphere 30 via the nonreturn valve 41 until the pressure drops below the pressure in the inhalation line 42. The patient 34 can breath spontaneously at any pressure level with this circuit arrangement.

Figure 4:
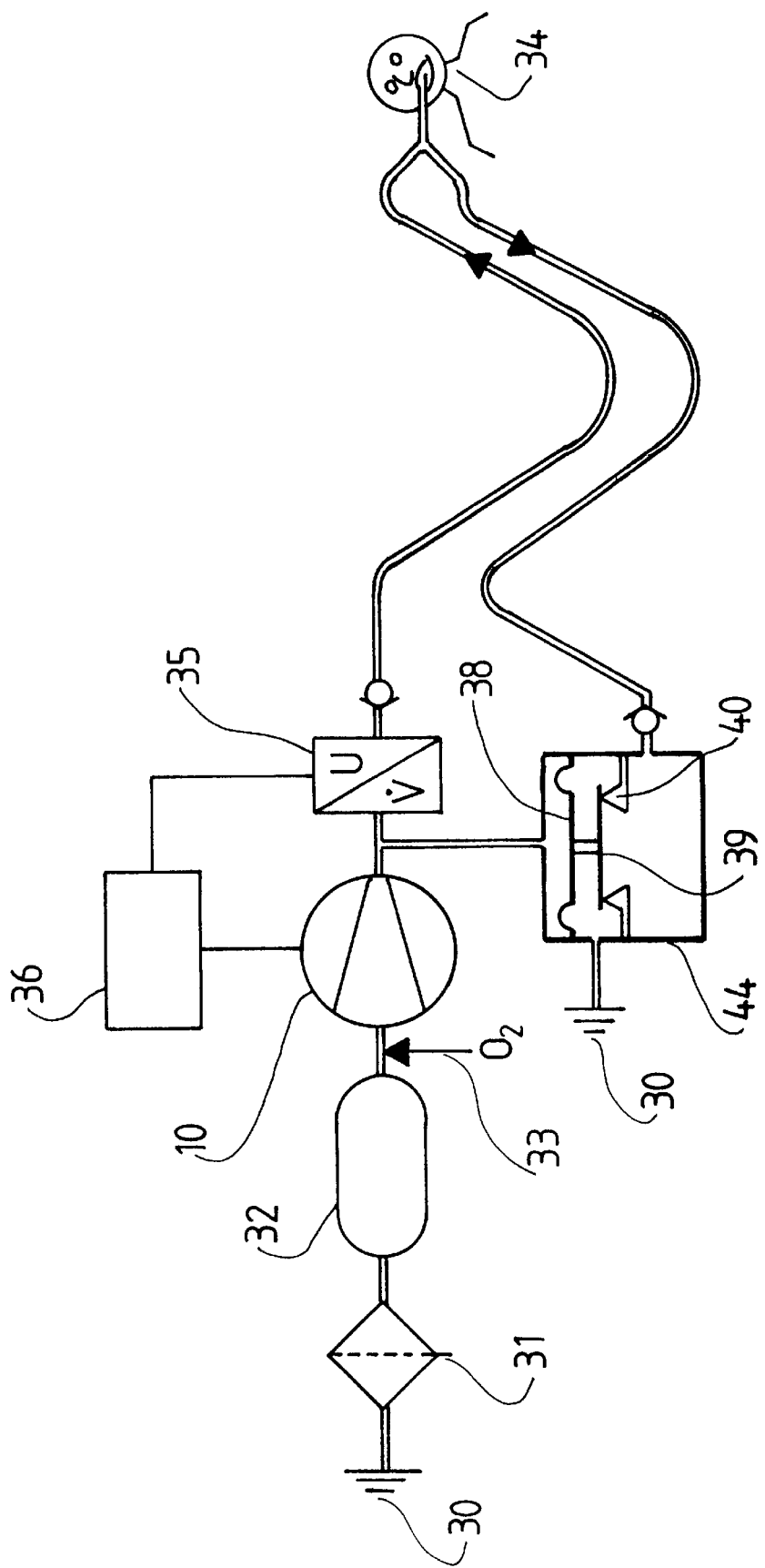
FIG. 4 a circuit for intensive-care respiration.

FIG. 4 shows a circuit for intensive-care respiration. The exhalation valve 44 corresponds to the patient valve 38, 39, 40 in FIG. 3. Only exhaled gas flows through the exhalation valve 44, and all other functions are the same as in FIG. 3.

Figure 5:
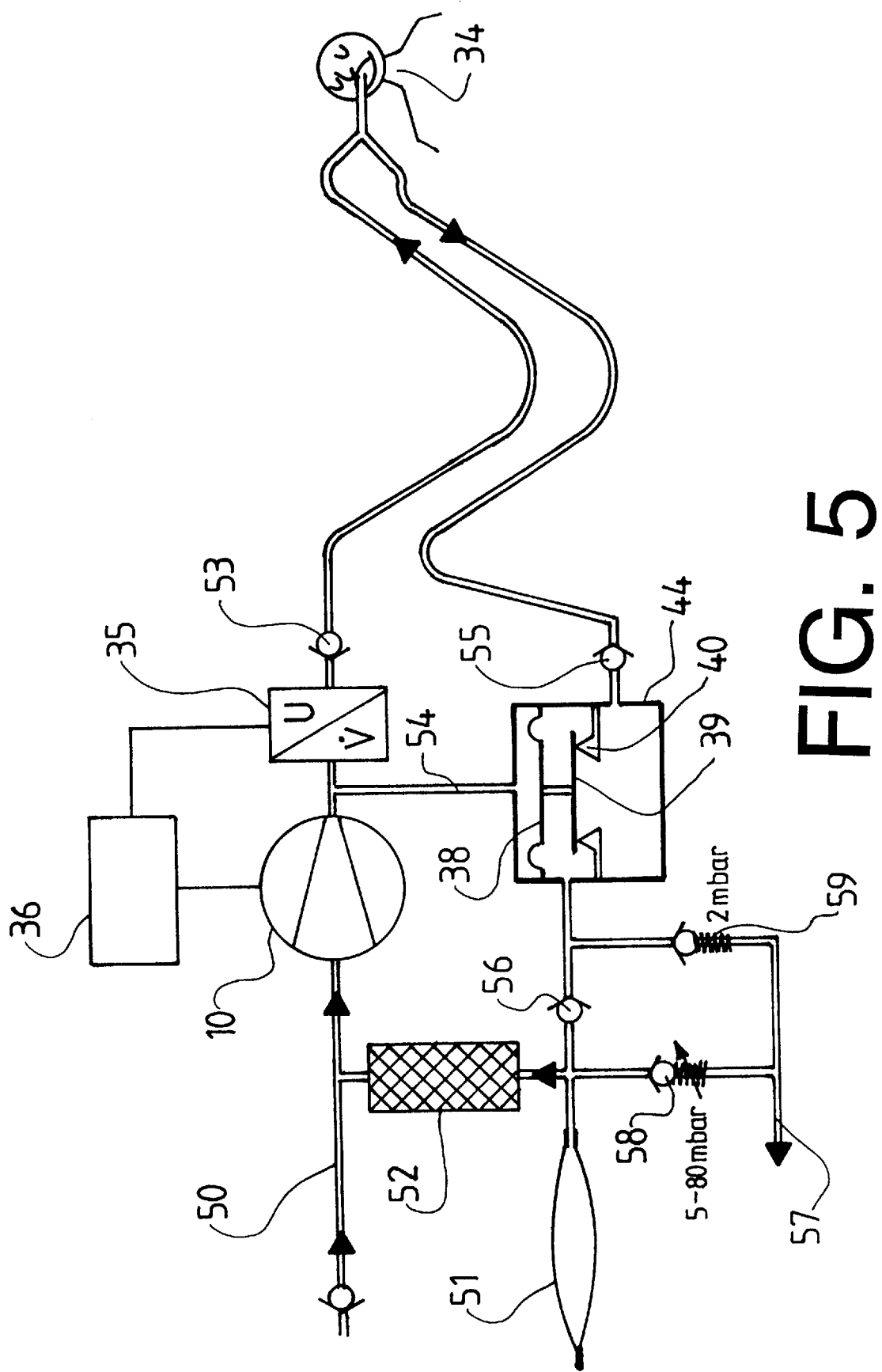
FIG. 5 is a first circuit for anesthetic respiration.

FIG. 5 shows a circuit of the radial flow compressor 10 for anesthesia. During inhalation, the radial flow compressor 10 with the drive motor draws in a mixture of oxygen, laughing gas and evaporated anesthetic from the fresh gas line 50 equipped with a nonreturn valve and breathing gas from the manual respiration bag 51 via the carbon dioxide absorber 52. The inhaled gas flows to the patient 34 through the nonreturn valve 53 if the pressure is lower there than at the compressor and the exhalation valve 44 is consequently closed via the control line 54. As soon as the pressure ratios reverse, the exhalation valve 44 opens and the gas flows into the manual respiration bag 51 through the nonreturn valves 55 and 56 until the bag 51 is filled completely and a pressure of 2 mbar is exceeded in it. The exhaled gas then flows into the anesthetic gas escape line 57 via the nonreturn valve 59 until the next inhalation begins. The circuit is driven by the manual respiration bag 51 during the manual respiration, and the valve 58 limits the pressure in the airways. Manual respiration at an increased pressure level is possible with the radial flow compressor 10 running. The inhalation flow is measured in the flow sensor 35, and the measured values may be used in the compressor electronic unit 36 with drive motor for controlling volume-based forms of respiration. The patient 34 can breath spontaneously at any pressure level with this circuit.

Figure 6:
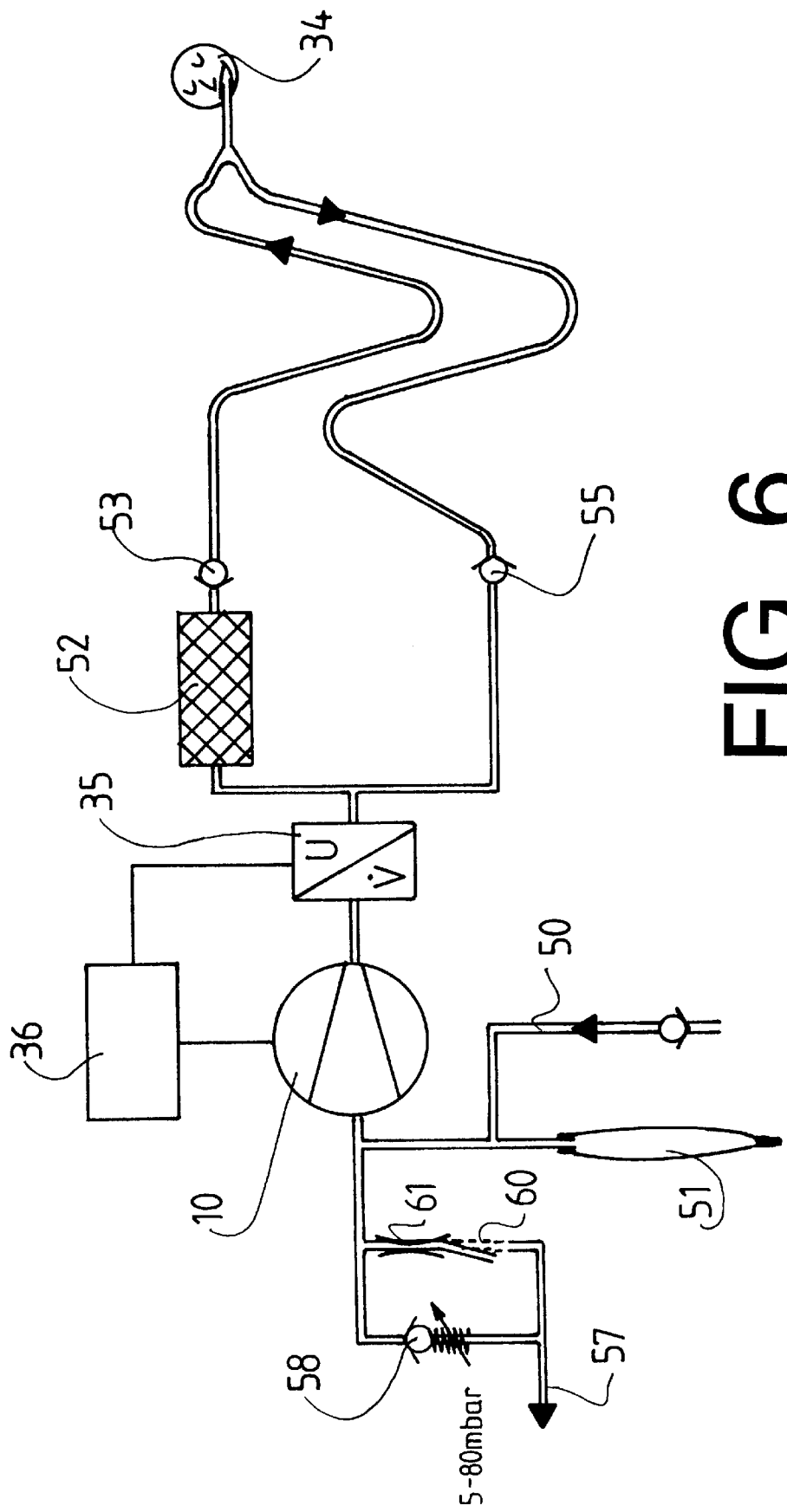
FIG. 6 is a second circuit for anesthetic respiration.
Figure 7:
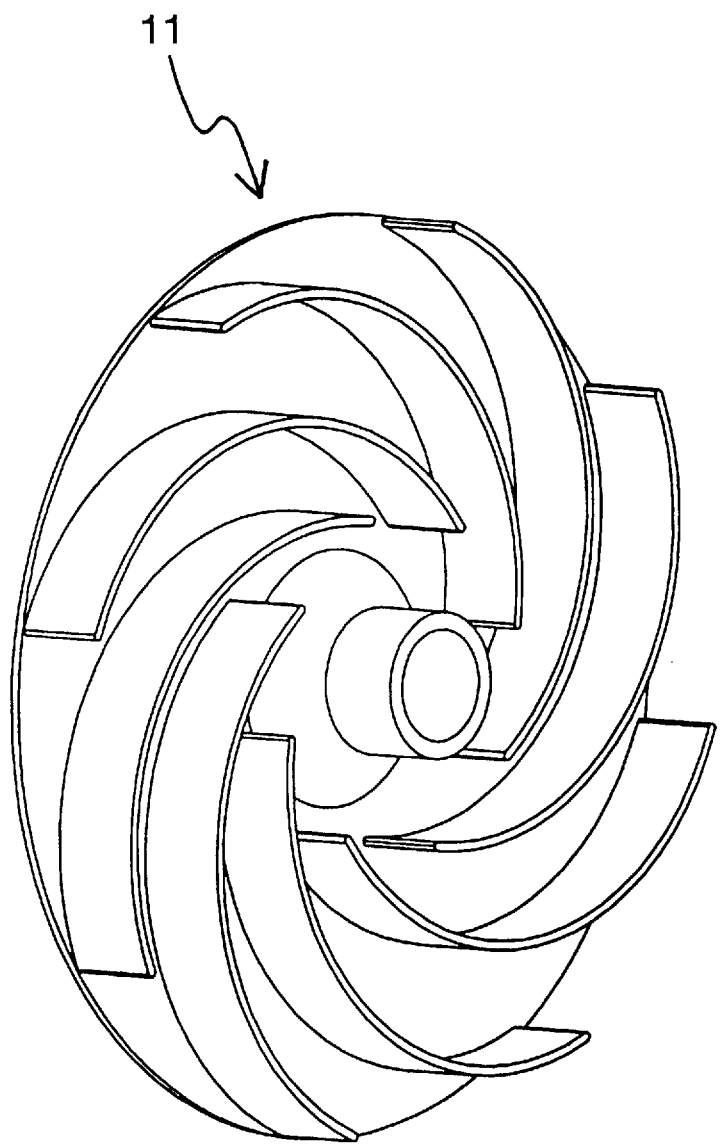
FIG. 7 is a perspective view of the impeller.

FIG. 6 shows a second circuit of the radial flow compressor 10 for anesthesia. During inhalation, the radial flow compressor 10 draws in a mixture of oxygen, laughing gas and evaporated anesthetic from the fresh gas line 50 and breathing gas from the manual respiration bag 51. The breathing gas to be breathed in reaches the patient 34 via the carbon dioxide absorber 52 and through the nonreturn valve 53 if the pressure is lower there than at the radial flow compressor 10. As soon as the pressure ratios reverse, the gas flows into the manual respiration bag 51 through the nonreturn valve 55 and through the radial flow compressor 10. The circuit is relieved into the anesthetic gas escape line 57 via the resistance 61, i.e., the switch 60 must be in the position indicated by broken line for automatic respiration. The circuit is driven by the manual respiration bag 51 during the manual respiration, and the valve 58 limits the pressure in the airways. Manual respiration at an increased pressure level is possible with the radial flow compressor 10 running. The inhalation flow is measured in the flow sensor 35, and the measured data may be used in the compressor electronic unit 36 equipped with drive motor for controlling volume-based forms of respiration. The patient 34 can breath spontaneously at any pressure level with this circuit as well. FIG. 7 shows the appearance, in a perspective view of the preferred impeller 11 (not to scale). The impeller 7 includes a central cylindrical portion defining an opening. The blades 13 start at a point spaced from the blades 13 and terminate at the edge of the impeller 11.

While specific embodiments of the invention has been shown and described in detail to illustrate the application of the principles of the invention, it will be understood that the invention may be embodied otherwise without departing from such principles.

What is claimed is:

1. A medical breathing system gas delivery arrangement, comprising:
    a radial flow compressor with
        an impeller with bent-backwards blades,
        a housing, said compressor impeller being arranged in said housing, said housing having a gas inlet located in an area of an axis of rotation of said compressor impeller, and said blades extending from said gas inlet to a circular outer edge of said compressor impeller and said blades terminating nearly tangentially at said circular outer edge, said housing defining a gas flow path between an outer extent of said compressor impeller and an inner wall of said housing and passing over into a gas outlet in a direction of gas flow, and
        an electric motor driving said compressor impeller, said compressor impeller having a radius of up to 40 mm and a mass moment of inertia of up to about $4 \times 10^{-6}$ kg×m$^2$;
    control means for controlling said motor to provide a respiration gas flow from said radial flow compressor.

2. The medical breathing system gas delivery arrangement in accordance with claim 1, wherein said impeller has at least 6 and preferably 8 to 12 blades, said blades having a height of at least 4 mm in parallel to the axis of rotation of the said compressor impeller and said compressor impeller has a radius of up to 25 mm and a mass moment of inertia of up to about $2 \times 10^{-6}$ kg×m$^2$.

3. The medical breathing system gas delivery arrangement in accordance with claim 1, wherein said compressor operates in a differential pressure range of up to 100 mbar, measured between said gas inlet and said gas outlet, at a gas volume flow rate of up to 200 L per minute.

4. The medical breathing system gas delivery arrangement in accordance with claim 1, further comprising:
    a gas storage space connected to said radial flow compressor and arranged upstream of said radial flow compressor;
    an ambient air connection connected to said gas storage space;
    an oxygen feed between said storage space and said radial flow compressor via a line;
    a supply line connected to said outlet of said radial flow compressor;
    a flow sensor disposed downstream of said radial flow compressor for monitoring flow in said supply line;
    an electronic unit as said control means and connected to said sensor for controlling said radial flow compressor;
    a nonreturn valve disposed in said supply line;
    a downstream exhalation valve connected to said supply line;
    a non return valve connected to said exhalation valve, said non return valve providing said exhalation valve with a connection to ambient air via said nonreturn valve; and
    a patient connection connected to said exhalation valve, wherein the arrangement forms a respirator.

5. The medical breathing system gas delivery arrangement in accordance with claim 1, further comprising:
    a gas storage space connected to said radial flow compressor and arranged upstream of said radial flow compressor;
    an ambient air connection connected to said gas storage space;
    an oxygen feed between said storage space and said radial flow compressor via a line;

a supply line connected to said outlet of said radial flow compressor;

a flow sensor disposed downstream of said radial flow compressor for monitoring flow in said supply line;

an electronic unit as said control means and connected to said sensor for controlling said radial flow compressor;

an inhalation line joining said flow sensor and having a nonreturn valve to a patient connection;

an exhalation line with a nonreturn valve to an exhalation valve, through which only exhaled gas flows, said exhalation valve ambient air connection connected to ambient air and a connection to said supply line and said outlet of said radial flow compressor, wherein said arrangement forms a respirator.

6. The medical breathing system gas delivery arrangement in accordance with claim 1, further comprising:

a fresh gas line with nonreturn valve, said fresh gas line being connected to said radial flow compressor;

a supply line connected to said outlet of said radial flow compressor;

a flow sensor for sensing flow in said supply line downstream of the said radial flow compressor;

an electronic unit as said control means and connected to said supply line for controlling said radial flow compressor, said supply line being joined by an inhalation line with a nonreturn valve, said inhalation line for connection to a patient;

an exhalation line with a nonreturn valve;

an exhalation valve connected to said exhalation line;

an anesthetic gas escape line connected to said exhalation valve via at least one nonreturn valve; and in parallel to said anesthetic escape line, a fresh gas line connected to said exhalation valve via a manual respiration bag as well as a carbon dioxide absorber, wherein said arrangement forms an anesthesia apparatus.

7. The medical breathing system gas delivery arrangement in accordance with claim 1, further comprising:

a fresh gas line with a nonreturn valve and with a manual respiration bag;

an anaesthetic gas escape line with a nonreturn valve and with a parallel flow resistance on an inlet side, said fresh gas line and said anaesthetic gas escape line being arranged upstream of said radial flow compressor;

a supply line connected to said outlet of said radial flow compressor;

a flow sensor for sensing flow in said supply line downstream of the said radial flow compressor;

an electronic unit as said control means and connected to said supply line for controlling said radial flow compressor;

an inhalation line leading to said patient with a carbon dioxide absorber and a nonreturn valve; and an exhalation line leading away from said patient with a nonreturn valve, said inhalation line and said exhalation line being connected to said supply line, arranged downstream of said radial flow compressor, wherein said arrangement forms an anesthesia apparatus.

8. The medical breathing system in accordance with claim 1, further comprising:

a flow sensor means for measuring gas flow from said compressor, said control means reading said flow sensor and providing said respiratory gas flow based on measured gas flow from said flow sensor.

9. The medical breathing system in accordance with claim 1, further comprising:

patient connection means connected to said compressor for respiration of a patient, wherein the system forms one of a respirator and an anesthesia apparatus.

10. A gas delivery arrangement, comprising:

a radial flow compressor with
an impeller with bent-backwards blades,
a housing, said compressor impeller being arranged in said housing, said housing having a gas inlet located in an area of an axis of rotation of said compressor impeller, and said blades extending from said gas inlet to a circular outer edge of said compressor impeller and said blades terminating nearly tangentially at said circular outer edge, said housing defining a gas flow path between an outer extent of said compressor impeller and an inner wall of said housing and passing over into a gas outlet in a direction of gas flow, and
an electric motor driving said compressor impeller, said compressor impeller having a radius of up to 40 mm and a mass moment of inertia of up to about $4 \times 10^{-6}$ kg$\times$m$^2$;

a gas storage space connected to said radial flow compressor and arranged upstream of said radial flow compressor;

an ambient air connection connected to said gas storage space;

an oxygen feed between said storage space and said radial flow compressor via a line;

a supply line connected to said outlet of said radial flow compressor;

a flow sensor disposed downstream of said radial flow compressor for monitoring flow in said supply line;

an electronic unit connected to said sensor for controlling said radial flow compressor; a nonreturn valve disposed in said supply line;

a downstream exhalation valve connected to said supply line;

a non return valve connected to said exhalation valve, said non return valve providing said exhalation valve with a connection to ambient air via said nonreturn valve; and a patient connection connected to said exhalation valve, wherein the arrangement forms a respirator.

11. A gas delivery arrangement, comprising:

a radial flow compressor with
an impeller with bent-backwards blades,
a housing, said compressor impeller being arranged in said housing, said housing having a gas inlet located in an area of an axis of rotation of said compressor impeller, and said blades extending from said gas inlet to a circular outer edge of said compressor impeller and said blades terminating nearly tangentially at said circular outer edge, said housing defining a gas flow path between an outer extent of said compressor impeller and an inner wall of said housing and passing over into a gas outlet in a direction of gas flow, and
an electric motor driving said compressor impeller, said compressor impeller having a radius of up to 40 mm and a mass moment of inertia of up to about $4 \times 10^{-6}$ kg$\times$m$^2$;

a gas storage space connected to said radial flow compressor and arranged upstream of said radial flow compressor;

an ambient air connection connected to said gas storage space;

an oxygen feed between said storage space and said radial flow compressor via a line;

a supply line connected to said outlet of said radial flow compressor;

a flow sensor disposed downstream of said radial flow compressor for monitoring flow in said supply line;

an electronic unit connected to said sensor for controlling said radial flow compressor;

an inhalation line joining said flow sensor and having a nonreturn valve to a patient connection;

an exhalation line with a nonreturn valve to an exhalation valve, through which only exhaled gas flows, said exhalation valve ambient air connection connected to ambient air and a connection to said supply line and said outlet of said radial flow compressor, wherein said arrangement forms a respirator.

* * * * *

UNITED STATES PATENT AND TRADEMARK OFFICE
CERTIFICATE OF CORRECTION

PATENT NO. : 5,875,783
DATED : March 2, 1999
INVENTOR(S) : Götz KULLIK

It is certified that error appears in the above-indentified patent and that said Letters Patent is hereby corrected as shown below:

On the title page, the priority data should read as follows:

--[30] Foreign Application Priority Data

April 9, 1997  [DE]  Germany ..... 19714644.9--.

Signed and Sealed this

Twenty-third Day of November, 1999

Attest:

Q. TODD DICKINSON

*Attesting Officer*   *Acting Commissioner of Patents and Trademarks*